US008183212B2

(12) United States Patent
Fujii et al.

(10) Patent No.: US 8,183,212 B2
(45) Date of Patent: May 22, 2012

(54) COMPOUND HAVING GPR54 AGONISTIC ACTIVITY

(75) Inventors: Nobutaka Fujii, Kyoto (JP); Shinya Oishi, Kyoto (JP); Kenji Tomita, Kyoto (JP); Ayumu Niida, Kyoto (JP)

(73) Assignees: Kyoto University, Kyoto (JP); Takeda Phamaceutical Company Limited, Osaka (JP)

( * ) Notice: Subject to any disclaimer, the term of this patent is extended or adjusted under 35 U.S.C. 154(b) by 538 days.

(21) Appl. No.: 12/298,200

(22) PCT Filed: Oct. 24, 2006

(86) PCT No.: PCT/JP2006/321597
§ 371 (c)(1),
(2), (4) Date: Apr. 6, 2009

(87) PCT Pub. No.: WO2007/125619
PCT Pub. Date: Nov. 8, 2007

(65) Prior Publication Data
US 2010/0160241 A1    Jun. 24, 2010

(30) Foreign Application Priority Data
Apr. 26, 2006  (JP) .................... 2006-122305

(51) Int. Cl.
*A61K 38/08* (2006.01)
*C07K 5/00* (2006.01)
*C07K 7/00* (2006.01)
*C07K 16/00* (2006.01)
*C07K 17/00* (2006.01)

(52) U.S. Cl. ...................... 514/21.8; 530/330
(58) Field of Classification Search .......... None
See application file for complete search history.

(56) References Cited

U.S. PATENT DOCUMENTS

| 6,800,611 B2* | 10/2004 | Fujii et al. ............ 514/1.3 |
| 7,625,869 B2* | 12/2009 | Kitada et al. ............ 514/1.1 |
| 7,786,083 B2* | 8/2010 | Asami et al. ........... 514/19.8 |
| 2006/0241051 A1* | 10/2006 | Kitada et al. ............. 514/15 |
| 2008/0215700 A1* | 9/2008 | Pillar et al. ............. 709/212 |
| 2008/0312155 A1* | 12/2008 | Kitada et al. ............. 514/15 |
| 2009/0246140 A1* | 10/2009 | Covalin et al. ............ 424/9.3 |
| 2009/0298765 A1* | 12/2009 | Kitada et al. ............. 514/12 |
| 2009/0318365 A1* | 12/2009 | Kitada et al. ............. 514/15 |
| 2011/0039786 A1* | 2/2011 | Fujii et al. ............. 514/17.8 |
| 2011/0059888 A1* | 3/2011 | Asami et al. ............ 514/6.8 |

FOREIGN PATENT DOCUMENTS
WO   WO-2004/060264 A2   7/2004

OTHER PUBLICATIONS

Tetsuya, Ohtaki et al., "Metastasis suppressor gene KISS-1 encodes peptide ligand of a G-proein-coupled receptor," Nature, vol. 411, May 31, 2001, pp. 613-617.
Masui, Toshihiko et al., "Metastin and its variant forms suppress migration of pancreatic cancer cells," Biochemica and Biophysical Research Communications vol. 315 (2004), pp. 85-92.
Horikoshi, Yasuko et al., "Dramatic Elevation of Plasma Metastin Concentrations in Human Pregnancy: Metastin as a Novel Placenta-Derived Hormone in Humans," The Journal of Clinical Endocrinology & Metabolism, vol. 88(2), pp. 914-919.
Tomita, Kenji et al., "Structure-Activity Relationship Study on hOT7T175 Agonists with RW-aminde," 42nd Japanese Peptide Symposium Koen Yoshishu, (Oct. 25, 2005), Endai Bango P-030.
24th Medicinal Chemistry Symposium Koen Yoshishu, (Nov. 10, 2005), p. 94, Endai Bando 1P-25 and English Abstract thereof.
Proceedings of the 126th Annual Meeting of the Pharmaceutical Society of Japan (Mar. 28-30, 2008), Program/Yoshishu, Endai Bango P30{S]pm-583 and English Translation thereof.

* cited by examiner

*Primary Examiner* — Marcela M Cordero Garcia
(74) *Attorney, Agent, or Firm* — Edwards Wildman Palmer LLP

(57) ABSTRACT

The present invention provides a compound represented by the following formula (1);

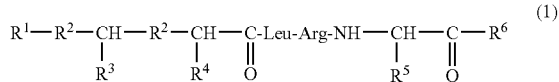

wherein
$R^1$ is an aryl group etc.;
$R^2$ is —CO—NH— etc.;
$R^3$ is a methyl group having an aromatic group or a cycloalkyl group;
$R^4$ is a hydrogen atom etc.;
$R^5$ is a methyl group having an aromatic group; and
$R^6$ is an amino group or an N-alkyl substituted amino group, having a low-molecular weight and a superior GPR54 agonist activity, and a pharmaceutical composition containing the compound.

9 Claims, No Drawings

COMPOUND HAVING GPR54 AGONISTIC ACTIVITY

TECHNICAL FIELD

CROSS-REFERENCES TO RELATED APPLICATIONS

This application is a U.S. national phase application, pursuant to 35 U.S.C. §371, of PCT/JP2006/321597, filed Oct. 24, 2006, designating the United States and published on Nov. 8, 2007 as WO 2007/125619 A1, which claims priority to Japanese application 2006-122305, filed Apr. 26, 2006. The entire contents of the aforementioned patent applications are incorporated herein by this reference.

The present invention relates to a compound having a GPR54 agonist activity.

BACKGROUND ART

Metastin is a C-terminal amide type single chain peptide consisting of 54 amino acid residues, and was found as an endogenous ligand of seven-transmembrane receptor GPR54 coupled with Gq protein. The amino acid sequence of metastin matches with the amino acid sequence of a gene product fragment of human cancer metastasis suppressor gene KiSS-1. In fact, a report has documented that metastin indeed significantly inhibited metastasis of lung transitional GPR54-expressing melanoma (e.g., Ohtaki T, Shintani Y, Honda S, Matsumoto H, Hori A, Kanehashi K, Terao Y, Kumano S, Takatsu Y, Masuda Y, Ishibashi Y, Watanabe T, Asada M, Yamada T, Suenaga M, Kitada C, Usuki S, Kurokawa T, Onda H, Nishimura O, Fujino M. Nature. 2001, 411, 613-7.). Likewise, it has been clarified that metastin also suppresses the mobility of GPR54-expressing pancreatic cancer cells (e.g., Masui T, Doi R, Mori T, Toyoda E, Koizumi M, Kami K, Ito D, Peiper S C, Broach J R, Oishi S, Niida A, Fujii N, Imamura M. Biochem Biophys Res Commun. 2004 Feb. 27; 315(1): 85-92.). In addition, since metastin is isolated from human placenta, and its blood concentration is markedly high in the gastation period, and further, since GPR54 is strongly expressed in the pituitary gland and the like, the role of the metastin/GPR54 system in the control of sexual function is drawing attention. In recent years, moreover, it has been reported that the action of an agonist on the intracerebral GPR54 promotes release of sex hormones such as gonadotropin and the like, and the functional deficiency of GPR54 causes the sexual hypofunction. Therefore, the metastin/GPR54 system is a highly attractive drug discovery target for both the suppression of cancer metastasis and sexual functional disease.

The present inventors have initiated a creative investigation of a low molecular agonist with the aim to develop a novel chemotherapeutic agent targeting GPR54. As a first step, the present inventors conducted investigation to lower the molecular weight of metastin using metastin (45-54) (SEQ ID NO: 1) as a base skeleton which shows about 10-fold GPR54 binding affinity as compared to full-length metastin. Based on the information in the literatures, they configured an RW-amide skeleton on the C-terminal side, designed a short chain peptide having a basic functional group on the N-terminal side via a spacer, and performed synthesis, activity evaluation of various derivatives. As a result, they have found 5 residue peptide derivative FM052a1 (molecular weight 992.2: SEQ ID NO: 2) and FM053a2 (molecular weight B52.0: SEQ ID NO: 3), having a GPR54 agonist activity equivalent to that of metastin (molecular weight 5857.5) and drastically low molecular weights (e.g., Horikoshi, Y.; Matsumoto, H.; Takatsu, Y.; Ohtaki, T.; Kitada, C.; Usuki, S.; Fujino, M. J. Clin. Endocrinol. Metab. 2003, 88, 914-919.). The present inventors have tried to develop novel GPR54 agonist having still higher activity.

DISCLOSURE OF THE INVENTION

The present invention mainly aims to provide a compound having a low-molecular weight and a superior GPR54 agonist activity, as well as a pharmaceutical composition comprising the compound.

The present inventors have conducted intensive studies of the above-mentioned pentapeptides (FM052a1 and FM053a2) and found that a pentapeptide modified to have, on the N-terminal, (i) an aryl group or an aryl group having electron-withdrawing properties as a whole, (ii) a substituted or unsubstituted aromatic heterocyclic group comprising at least one kind of hetero atom selected from the group consisting of a nitrogen atom, an oxygen atom and a sulfur atom, or (iii) an aryl group substituted by 1 to 3 electron-donating groups selected from the group consisting of a lower alkoxy group, a hydroxy lower alkyl group, an amino lower alkyl group, a lower alkanoylamino lower alkyl group, a hydroxy substituted phenylcarbonyloxy group, an amino group and a hydroxyl group has a superior GPR54 agonist activity. The present invention was obtained as a result of further studies based on the above-mentioned finding.

The present invention provides the following compound and a pharmaceutical composition comprising said compound.

[1] A compound represented by the following formula (1):

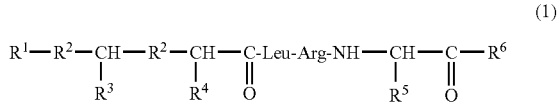

wherein
$R^1$ is
(i) an aryl group or an aryl group having electron-withdrawing properties as a whole,
(ii) a substituted or unsubstituted aromatic heterocyclic group comprising at least one kind of hetero atom selected from the group consisting of a nitrogen atom, an oxygen atom and a sulfur atom, or
(iii) an aryl group substituted by 1 to 3 electron-donating groups selected from the group consisting of a lower alkoxy group, a hydroxy lower alkyl group, an amino lower alkyl group, a lower alkanoylamino lower alkyl group, a hydroxy substituted phenylcarbonyloxy group, an amino group and a hydroxyl group;
$R^2$ is any one kind selected from the group consisting of —CO—NH—, —CH=CH—, —SO$_2$—NH— and —CH$_2$—NH—;
$R^3$ is a methyl group having an aromatic group or a cycloalkyl group;
$R^4$ is any one kind selected from the group consisting of a hydrogen atom, a methyl group, a phenyl group and a benzyl group;
when $R^2$ is —CO—NH—, —SO$_2$—NH— or —CH$_2$—NH— and the nitrogen atom of $R^2$ is bonded to $R^4$, then —$R^2$—CHR$^4$— optionally forms

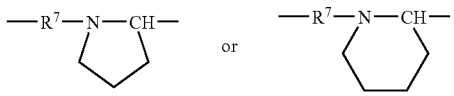

wherein R⁷ is —CO—, —SO₂— or —CH₂—;
R⁵ is a methyl group having an aromatic group; and
R⁶ is an amino group or an N-alkyl-substituted amino group.

[2] The compound of the above-mentioned [1], wherein R¹ is any one kind selected from the group consisting of a 2-pyrrolyl group, a 4-methoxyphenyl group, a 4-chlorophenyl group and a 4-fluorophenyl group.

[3] The compound of the above-mentioned [1] or [2], wherein R³ is any one kind selected from the group consisting of a benzyl group, a naphthylmethyl group and a cyclohexylmethyl group.

[4] The compound of any of the above-mentioned [1]-[3], wherein R⁴ is a hydrogen atom.

[5] The compound of any of the above-mentioned [1]-[4], wherein R⁵ is any one kind selected from the group consisting of a 3-indolylmethyl group, a naphthylmethyl group, a benzyl group and a hydroxybenzyl group.

[6] A pharmaceutical composition comprising a compound of any of the above-mentioned [1]-[5], and a pharmaceutically acceptable excipient, a diluent or a carrier.

[7] The pharmaceutical composition of the above-mentioned [6], wherein the activation of GPR54 is for a prophylactically or therapeutically effective disease.

[8] A cancer metastasis suppressor comprising a compound of any of the above-mentioned [1]-[5].

[9] The metastasis suppressor of the above-mentioned [8], wherein the cancer is melanoma or pancreatic cancer.

[10] A therapeutic agent for infertility comprising the compound of any of the above-mentioned [1]-[5].

DETAILED DESCRIPTION OF THE INVENTION

The compound of the present invention and a pharmaceutical composition comprising said compound are explained in the following.

In the peptide described in the present specification, in accordance with the conventional practice of peptide marking, the left end is N-terminal (amino terminal) and the right end is C-terminal (carboxyl terminal).

In the present specification, when amino acids are indicated with abbreviations, they are based on the abbreviations according to IUPAC-IUB Commission on Biochemical Nomenclature or conventional abbreviations used in the pertinent field. Thus, Phe means phenylalanine, Gly means glycine, Leu means leucine, Arg means arginine, and Trp means tryptophan.

1. Compound having GPR54 Agonist Activity

The compound of the present invention is represented by the following formula (1):

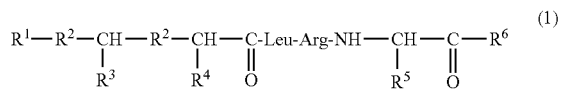

wherein
R¹ is
(i) an aryl group or an aryl group having electron-withdrawing properties as a whole,
(ii) a substituted or unsubstituted aromatic heterocyclic group comprising at least one kind of hetero atom selected from the group consisting of a nitrogen atom, an oxygen atom and a sulfur atom, or
(iii) an aryl group substituted by 1 to 3 electron-donating groups selected from the group consisting of a lower alkoxy group, a hydroxy lower alkyl group, an amino lower alkyl group, a lower alkanoylamino lower alkyl group, a hydroxy substituted phenylcarbonyloxy group, an amino group and a hydroxyl group;

R² is any one kind selected from the group consisting of —CO—NH—, —CH=CH—, —SO₂—NH— and —CH₂—NH—;

R³ is a methyl group having an aromatic group or a cycloalkyl group;

R⁴ is any one kind selected from the group consisting of a hydrogen atom, a methyl group, a phenyl group and a benzyl group;

when R² is —CO—NH—, —SO₂—NH— or —CH₂—NH— and the nitrogen atom of R² is bonded to R⁴, then —R²—CHR⁴— optionally forms

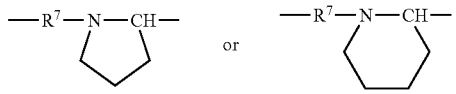

wherein R⁷ is —CO—, —SO₂— or —CH₂—;
R⁵ is a methyl group having an aromatic group; and
R⁶ is an amino group or an N-alkyl-substituted amino group.

(i) An Aryl Group or an Aryl Group having Electron-Withdrawing Properties as a Whole In the present invention, examples of the aryl group include a phenyl group, a naphthyl group and the like, and a phenyl group is preferable. In the present invention, the aryl group having electron-withdrawing properties as a whole means said aryl group having 1 to 3 as necessary, preferably 1, electron-withdrawing substituent(s). When two or more substituents are present on the aryl group, the substituents are the same or different. In addition, the aforementioned aryl group means an aryl group having only an electron-withdrawing group, or an aryl group having both an electron-withdrawing group and an electron-donating group wherein the effect of the electron-withdrawing property is higher in R¹ as a whole.

Examples of the above-mentioned electron-withdrawing substituent include halogen such as fluorine, chlorine, bromine, iodine and the like, —NO₂, —SO₃H, —SO₂—, —CHO, —CF₃, R—CO—, —CN and the like. Preferred are halogen and a nitro group, more preferred are fluorine and chlorine, and particularly preferred is fluorine.

(ii) A Substituted or Unsubstituted Aromatic Heterocyclic Group Comprising at Least One Kind of Hetero Atom Selected from the Group Consisting of a Nitrogen Atom, an Oxygen Atom and a Sulfur Atom In the present invention, examples of the aromatic heterocyclic group containing at least one kind of hetero atom selected from the group consisting of a nitrogen atom, an oxygen atom and a sulfur atom include a 5-membered to 7-membered, preferably 5-membered or 6-membered, nitrogen-containing aromatic heterocyclic group and having 1 or 2 nitrogen atoms such as pyrrolyl group, imidazolyl group, pyrazolyl group, pyridyl group, pyrazinyl group, pyrimidinyl group, pyridazinyl group and the like; an oxygen-containing aromatic heterocyclic group such as furyl group and the like; and a sulfur-containing aromatic heterocyclic group such as thienyl group and the like. Of these, a 5-membered to 7-membered, preferably 5-membered or 6-membered aromatic heterocyclic group having 1 or 2 nitrogen atoms is preferable, and pyridyl group, pyrrolyl group, imidazolyl group and the like are more preferable.

Moreover, the above-mentioned aromatic heterocyclic group may contain 1-5, preferably 1-3, more preferably 1, substituent(s). The substituent is preferably an electric-withdrawing substituent, as mentioned above. Examples thereof include halogen such as fluorine, chlorine, bromine, iodine and the like, —NO$_2$, —SO$_3$H, —SO$_2$—, —CHO, —CF$_3$, R—CO—, —CN and the like. Preferred are halogen and a nitro group, more preferred is fluorine. When the above-mentioned aromatic heterocyclic group has two or more substituents, the substituents may be the same or different.

(iii) An Aryl Group Substituted by 1 to 3 Electron-Donating Groups

In the present invention, R$^1$ may be an aryl group substituted by 1 to 3 electron-donating groups. Here, the aryl group can be defined as in the above-mentioned (1). Examples of the electron-donating substituent include lower alkoxy group, hydroxy lower alkyl group, amino lower alkyl group, lower alkanoylamino lower alkyl group, hydroxy substituted phenylcarbonyloxy group, amino group, hydroxyl group and the like. When two or more substituents are present on the aryl group, the substituents are the same or different.

In the present invention, examples of the lower alkoxy group include a linear or branched chain alkoxy group having a carbon number of 1-6. Examples of the aforementioned lower alkoxy group include methoxy group, ethoxy group, propoxy group, isopropoxy group, butoxy group, isobutoxy group, sec-butoxy group, Cert-butoxy group, 2-methylpropoxy group, 3-methylpropoxy group, 2,2,2-trimethylmethoxy group, pentyloxy group, isopentyloxy group, hexyloxy group, isohexyloxy group and the like, with preference given to methoxy group.

In the present invention, examples of the hydroxy lower alkyl group include an alkyl group having a carbon number of 1-6 and a hydroxyl group. Examples of the aforementioned hydroxy lower alkyl group include hydroxymethyl group, hydroxyethyl group, hydroxypropyl group, hydroxybutyl group, hydroxypentyl group and the like, with preference given to hydroxymethyl group.

In the present invention, examples of the amino lower alkyl group include straight chain or branched chain alkyl group having a carbon number of 1-6, preferably 1-3, and an amino group. Examples of the aminoalkyl group having a carbon number of 1-6 include aminomethyl group, aminoethyl group, amino n-propyl group, amino i-propyl group, amino n-butyl group, amino sec-butyl group, amino tert-butyl group, amino n-pentyl group, amino i-pentyl group, amino tert-pentyl group, amino neopentyl group, amino 2-pentyl group, amino 3-pentyl group, amino n-hexyl group and amino 2-hexyl group and the like. Of these, aminomethyl group, aminoethyl group, amino n-propyl group and amino i-propyl group are preferable.

In the present invention, examples of the lower alkanoylamino lower alkyl group include the aforementioned amino lower alkyl group having 1 or 2 alkanoyl groups having a carbon number of 1-6 on the amino group. Examples of the lower alkanoylamino lower alkyl group include N-acetylaminomethyl group, formylaminomethyl group, propionylaminomethyl group, pentylcarbonylaminomethyl group and the like, with preference given to an N-acetylaminomethyl group.

In the present invention, examples of the hydroxy substituted phenylcarbonyloxy group include a phenylcarbonyloxy group substituted by 1-5, preferably 1-3, more preferably 1, hydroxy group(s), which is preferably a 2-hydroxy-substituted phenylcarbonyloxy group.

In the above-mentioned (i)-(iii), the position of the substituent on the aryl group or aromatic heterocyclic group is not particularly limited. In the case of, for example, a phenyl group or a pyrimidyl group, GPR54 agonist activity is preferably high when the 4-position is substituted by a electron-withdrawing group such as a nitro group, fluorine, chlorine, bromine, iodine and the like. For the same reason as above, the 3-position of the aforementioned phenyl group or heterocyclic group is preferably free of modification. Moreover, it is preferable that any substituent has hydrogen at the meta-position, or a hydrogen atom is added to the carbon at the 3-position.

Examples of the preferable substituent group for R$^1$ in the compound of the present invention, from among the above-mentioned (i)-(iii), are shown below.

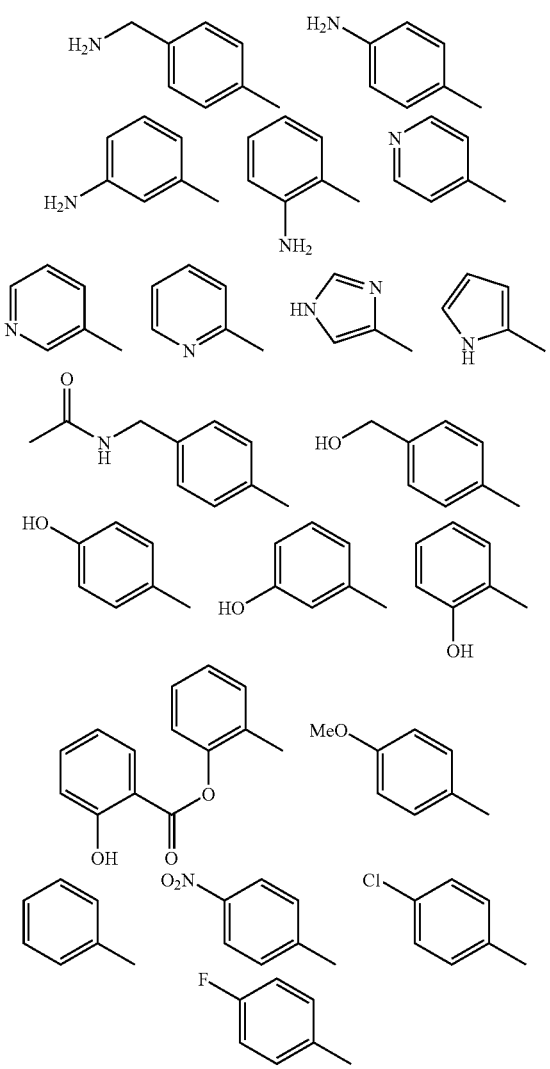

In the present invention, R$^2$ is —CO—NH—, —CH═CH—, —SO$_2$—NH—, —CH$_2$—NH— and the like. Of these, preferred is —CO—NH—.

R$^3$ is a methyl group having an aromatic group or a cycloalkyl group and, for example, a benzyl group, a naphthylmethyl group, a cyclohexylmethyl group and the like can be mentioned. When $R^3$ is a benzyl group or a naphthylmethyl group, superior GPR54 agonist activity can be preferably exhibited.

$R^4$ is a hydrogen atom, a methyl group, a phenyl group or a benzyl group, preferably a hydrogen atom.

When $R^2$ is —CO—NH—, —SO$_2$—NH— or —CH$_2$—NH—, $R^4$ may be bonded to a carbon atom, to which $R^4$ is bonded, and a nitrogen atom of $R^2$ to form a 5-membered or 6-membered heterocyclic group, and —$R^2$—CHR$^4$— is, for example, the following structure (wherein $R^7$ is —CO—, —SO$_2$— or —CH$_2$—).

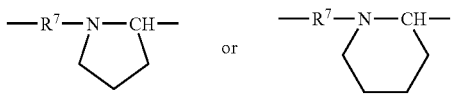

$R^5$ is a methyl group having an aromatic group. Examples of the methyl group having an aromatic group include 3-indolylmethyl group, naphthylmethyl group, benzyl group, hydroxybenzyl group and the like, preferably 3-indolylmethyl group and benzyl group.

The compound having a GPR54 agonist activity of the present invention shows markedly decreased GPR54 agonist activity when a carboxyl group is present at the C-terminal. Therefore, it is preferably of a C-terminal amide type. In the present invention, therefore, $R^6$ is an amino group; or an N-alkyl substituted amino group such as an N-methylamino group, an N-ethylamino group, an N-isopropylamino group, an N,N-dimethylamino group, an N,N-diethylamino group and the like, preferably an amino group.

As a preferable compound capable of exhibiting superior GPR54 agonist activity in the present invention, for example, the compound of the following formula (2) can be mentioned:

(2)

wherein $R^1$ is a 2-pyrrolyl group, a 4-methoxyphenyl group, a 4-chlorophenyl group or a 4-fluorophenyl group.

When $R^2$ is —CO—NH—, the compound of the present invention can be produced by a known polypeptide synthesis method, for example, Fmoc solid phase synthesis process, liquid phase synthesis process etc., and a known amino acid protecting method. Moreover, the compound of the present invention may be in the form of cyclic peptide. When cyclic peptide is to be synthesized, it can be synthesized according to a conventionally known method, for example, by extending the peptide chain, and obtained by intermolecular cyclization by azide method and the like. The thus-obtained compound of the present invention can be isolated and purified by a known means, such as extraction, recrystallization, various chromatographies (e.g., high performance liquid chromatography etc.), electrophoresis, countercurrent distribution and the like.

When $R^2$ is other than —CO—NH—, for example, it can be synthesized as in the following.

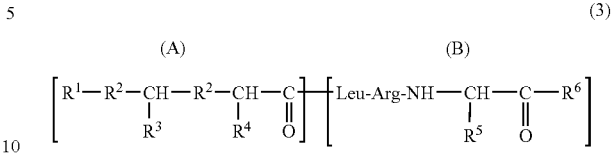

(3)

When $R^2$ is —CH═CH—, $R^1$—CH═CH—CHR$^3$—CO$_2$H or NH—CHR$^3$—CH═CH—CHR$^4$—CO$_2$H having a protecting group is prepared for moiety (A) in advance by a known method, which is then applied to a known polypeptide synthesis method to synthesize the compound.

When $R^2$ is —SO$_2$—NH—, the moiety (A) can be synthesized by a combination of a known polypeptide synthesis method and a known sulfonamide synthesis method using RSO$_2$Cl (5 eq.)-pyridine (5 eq.).

When $R^2$ is —CH$_2$—NH—, the moiety (A) can be synthesized by a combination of a known polypeptide synthesis method and a known substituted amine synthesis method using aldehyde (5 eq)-sodium acetoxyborohydride.

The moiety (B) in the compound of the present invention can be synthesized according to the aforementioned known polypeptide synthesis method.

By, condensation of moiety (A) and moiety (B) obtained as mentioned above by an amide bond according to a conventional method of peptide synthesis, the compound of the present invention can be obtained.

The compound of the present invention obtained as mentioned above has a GPR54 agonist activity. In the present invention, the agonist activity includes both activities of full agonist and partial agonist.

In addition, the compound represented by the above-mentioned formula (1) of the present invention encompasses isomers such as a geometric isomer, a stereoisomer, an optical isomer and the like.

2. Pharmaceutical Composition

The present invention also provides a pharmaceutical composition comprising the compound obtained by the above-mentioned method and/or a pharmaceutically acceptable salt thereof as an active ingredient, as well as a pharmaceutically acceptable excipient, a diluent or a carrier.

Examples of the pharmaceutically acceptable salt include physiologically acceptable salt with acid or base. Particularly, a physiologically acceptable acid addition salt is preferable. Examples of such salt include salts with inorganic acid such as hydrochloric acid, phosphoric acid, hydrobromic acid, sulfuric acid and the like, salts with organic acids such as acetic acid, formic acid, propionic acid, lactic acid, fumaric acid, maleic acid, succinic acid, tartaric acid, citric acid, malic acid, oxalic acid, benzoic acid, methanesulfonic acid, benzenesulfonic acid, hyaluronic acid, chondroitin sulfate and the like, and the like. One kind may be selected therefrom and used alone, or two or more kinds may be used in combination.

The compound of the present invention and/or the above-mentioned salt can be prepared as a pharmaceutical composition together with pharmaceutically acceptable conventionally known excipients, diluents, carriers and the like.

Examples of the excipient include starch, lactose, sucrose, mannit, carboxymethylcellulose, cornstarch, inorganic salts and the like, where one kind or two or more kinds can be used in combination.

Examples of the diluent include distilled water for injection, saline, aqueous glucose solution, vegetable oil for injection, propylene glycol, polyethylene glycol and the like, where one kind or two or more kinds can be used in combination.

Examples of the carrier include magnesium carbonate, magnesium stearate, talc, sucrose, lactose, pectin, dextrin, starch, gelatin, tragacanth, methylcellulose, carboxymethylcellulose sodium and the like, where one kind or two or more kinds can be used in combination.

Besides those mentioned above, as additives, for example, binder, disintegrant, surfactant, absorption promoter, moisturizing agent, adsorbent, lubricant, filler, extender, humectant, preservative, stabilizer, emulsifier, solubilizer, and salt for controlling osmotic pressure can be appropriately selected and used, according to the administration unit form of the obtained preparation. Moreover, the pharmaceutical composition of the present invention may be prepared by adding colorant, preservative, perfume, flavor, sweetening agent and the like as necessary.

Examples of the dosage form of the pharmaceutical composition of the present invention include, whether oral or parenteral (e.g., topical, rectal, intravenous administrations etc.), tablet (inclusive of sugar-coated tablet, film-coated tablet), powder, granule, capsule (inclusive of soft capsule), liquid, injection, suppository, sustained-release preparation and the like. When the form of the preparation is an injection, it can be administered intravenous, intramuscularly, subcutaneously, intraorgan, intranasally, intradermally, instillation, intracerebrally, intrarectally, vaginally and intraperitoneally, or can be administered to the inside of tumor, in the vicinity of tumor and the like or directly to the lesion.

When the pharmaceutical composition of the present invention is a liquid, water may be removed by freeze preservation, freeze-dry and the like and then preserved. A freeze-dry preparation is used by dissolving in distilled water for injection and the like when in use.

While the dose of the above-mentioned pharmaceutical composition can be determined appropriately according to the desired treatment effect, administration method, treatment period, age, sex and other conditions of patients and the like, it is generally about 1 pg-1 g, preferably about 1 pg-10 mg, more preferably about 1 pg-1 μg, still more preferably about 1 pg-500 ng, about 1 pg-50 ng, about 1 pg-1 ng, of the compound of the present invention, which is an active ingredient, per 1 kg body weight a day for one adult. The pharmaceutical composition of the present invention can be administered in one to several portions a day.

While the compound of the present invention can be used alone as an active ingredient, it can also be used in combination with other drugs. For a combined use with the compound of the present invention and a concomitant drug, the administration timing of the compound of the present invention and the concomitant drug is not limited. The compound of the present invention and the concomitant drug may be simultaneously administered to patients, or administered in a staggered manner. The dose of the concomitant drug may follow the dose employed clinically, and can appropriately determined in consideration of the subject of administration, administration route, disease, combination of pharmaceutical agents and the like.

The administration mode of the compound of the present invention and the concomitant drug is not particularly limited, and the compound of the present invention or a salt thereof and the concomitant drug only need to be combined simultaneously or in a staggered manner. Examples of such administration mode include the following:

(1) administration of a single preparation obtained by simultaneously processing the compound of the present invention and the concomitant drug, (2) simultaneous administration of two kinds of preparations of the compound of the present invention and the concomitant drug, which have been separately produced, by the same administration route, (3) administration of two kinds of preparations of the compound of the present invention and the concomitant drug, which have been separately produced, by the same administration route in a staggered manner, (4) simultaneous administration of two kinds of preparations of the compound of the present invention and the concomitant drug, which have been separately produced, by different administration routes, (5) administration of two kinds of preparations of the compound of the present invention and the concomitant drug, which have been separately produced, by different administration routes in a staggered manner (for example, administration in the order of the compound of the present invention and the concomitant drug, or in the reverse order) and the like.

Even when the concomitant drug and the pharmaceutical composition of the present invention are to be formulated as a single preparation, carrier, excipient and the like to be used may be similar to those used for the aforementioned pharmaceutical composition of the present invention. In addition, the mixing ratio or administration ratio of the concomitant drug to the compound of the present invention can be appropriately set according to the subject of administration, administration route, disease and the like.

The content of the concomitant drug in the combination drug of the present invention varies depending on the form of the preparation, and can be appropriately set based on the effect of the concomitant drug and the dose generally employed.

3. Application

The compound of the present invention specifically binds to GPR54, which is a seven-transmembrane receptor, to activate the receptor, and can enhance the action of its endogenous ligand, metastin (aka: kisspeptin). Accordingly, the compound of the present invention can be preferably used for diseases for which activation of GPR54 and accompanying enhancement of the action of metastin are effective for the prophylaxis or treatment (including treatments aiming at improvement, mitigation or cure of the symptoms) thereof. Specifically, the following diseases can be recited as examples.

Metastin is an endogenous ligand involved in the cancer metastasis, control of sexual function and the like.

It has been reported that metastin significantly inhibits metastasis of lung transitional GPR54-expressing melanoma cells, can suppress movement of pancreatic cancer cells and the like. Accordingly, a composition containing the compound of the present invention can be used as a metastasis suppressor of cancer such as melanoma, pancreatic cancer and the like.

Moreover, since the compound of the present invention has suppressive action for a sexual function degradation, it can also improve abnormal secretory regulation of sex hormones or gonadotropic hormones. While a imitative interpretation of the present invention is not intended, for example, since the compound of the present invention acts as a GPR54 agonist, cell chemotactic activity is suppressed, and nidation of fertilized egg is promoted, whereby an effect as an infecundity treatment drug is also expected.

Moreover, Jean-Marc Navenot et al., Cancer Res. 2004; 65:22. Nov. 15, 2005 made it clear that kisspeptin-10 (kp-10) derived from KiSS-i gene product activates GPR54 and suppresses the function of CXCR4. CXCR4 is a human type receptor protein encoded by CXCR4 gene as one of the G-protein-coupled receptor proteins, and is known to be involved in various diseases such as cancer metastasis or growth, chronic articular rheumatism, lung fibrosis, chronic lymphocytic B cell leukemia, HIV infection and the like.

Therefore, a pharmaceutical composition containing the compound of the present invention is expected to act suppressively on the diseases involving CXCR4. Examples of the diseases involving CXCR4 include AIDS, chronic lymphocytic B cell leukemia, cancer types expressing CXCR4, such as mouth cavity cancer, cancer of pharynx, lip cancer, tongue cancer, gingiva cancer, nasopharynx cancer, esophagus cancer, gastric cancer, small intestinal cancer, colorectal cancer including colon cancer, liver cancer, gallurinary bladder cancer, pancreatic cancer, nasal cavity cancer, lung cancer, osteosarcoma, soft tissue cancer, skin cancer, melanoma, breast cancer, uterine cancer, ovarian cancer, prostate cancer, testis cancer, penile cancer, urinary bladder cancer, kidney cancer, brain tumor, thyroid cancer, lymphoma, leukemia, chronic articular rheumatism and the like. Moreover, since involvement of CXCR4 in trauma such as burn and the like is also suggested, a pharmaceutical composition containing the compound of the present invention is considered to be applicable to cure of burn and the like.

EXAMPLES

The present invention is explained in more detail in the following by referring to Examples, which are not to be construed as limitative. In the present Examples, pentapeptide represented by the above-mentioned formula (1) wherein $R^2$ is —CONH— was prepared, and the GPR54 agonist activity thereof was measured.

1. Synthesis Method and Activity Evaluation Method of Compound having GPR54 Agonist Activity A compound having GPR54 agonist activity (pentapeptide derivative) was prepared according to a conventional Fmoc solid phase synthesis process using Rink-amide resin (Fields G B, Noble R L., Int J Pept Protein Res. 1990; 35, 161-214.). The GPR54 agonist activity of the obtained pentapeptide derivative was evaluated according to Flipr assay method wherein an increase in the intracellular $Ca^{2+}$ ion concentration due to receptor stimulation is measured as the fluorescence intensity. The activity value was calculated as the fluorescence intensity (% activity) with addition of $10^{-8}$M pentapeptide derivative relative to the fluorescence intensity with addition of $10^{-6}$M metastin (45-54) as 100%. In addition, the specific activity value relative to metastin (45-54) was calculated by Q (=$EC_{50}$ (compound)/$EC_{50}$ [metastin (45-54)]) wherein the concentration of the pentapeptide derivative showing 50% agonist activity was $EC_{50}$. Hereafter, the agonist activity was mainly compared based on the Q value.

In the studies until present, the present inventors have obtained pentapeptide derivatives FM052a1 (molecular weight 992.2) and FM053a2 (molecular weight 852.0), which have a GPR54 agonist activity equivalent to that of metastin (molecular weight 5857.5) and drastically reduced molecular weights (Niida, A et al, Bioorg. Med. Chem. Lett. 2006, 16, 134-137).

Compound 6, which is an N-terminal amino derivative free of both the picolyl groups of FM052a1, was prepared. The compound showed an activity almost equivalent to that of FM052a1 (Table I). Since compound 6 does not require an N-terminal modification step and is easily purified as compared to FM052a1, the following study of the structure activity correlation was conducted based mainly on compound 6.

TABLE I

Activity of pentapeptide derivative $R^x$-C<sub>6</sub>H<sub>4</sub>-C(=O)-Phe-Gly-Leu-Arg-Trp-NH<sub>2</sub>

| compound | $R^x$ | % activity[a] | $EC_{50}$ (nM)[a] | $Q^a$ |
|---|---|---|---|---|
| Metastin (45-54) | | 100 | 0.36-1.1 | 1.0 |
| 1 (FM052a) | N,N-bis-(2-picolyl)aminomethyl | 89 | 3.3 | 3.1 |
| 2 (FM053a) | guanidinomethyl | 94 | 1.4 | 1.6 |
| 6 | aminomethyl | 97 | 3.1 | 3.4 |

[a]Values were calculated based on Flipr assay.

Table I. discloses the structure sequence as SEQ ID NO: 26 and Metastin 1 and 2 as SEQ ID NOS 2 and 3, respectively, in order of appearance.

2. Correlation between Structure of Amino Acid Side Chain and GPR54 Agonist Activity To carefully examine the structural requirement of a compound having a GPR54 agonist activity, optimization of the amino acid residue ($Xaa^1$) at the 1-position of a pentapeptide derivative was considered (Table II). Compound 8, which is Compound 6 wherein $Phe^1$ is substituted by L-3-(2-naphthyl) alanine (Nal(2)) having a naphthalene ring which is an aromatic ring larger than the benzene ring, showed an activity about 4 times stronger than that of compound 6. From this, the presence of a large hydrophobic pocket was suggested in the side chain space of $Phe^1$.

TABLE II

| Compound | $Xaa^1$ | % activity[a] | $EC_{50}$ (nM)[a] | $Q^a$ |
|---|---|---|---|---|
| $Phe^1$ position | | | | |
| 6 | Phe | 97 | 3.1 | 3.4 |
| 8 | Nal(2) | 89 | 0.82 | 0.9 |

[a]Values were calculated based on Flipr assay.

3. Structure of N-Terminal Acyl Group and GPR54 Agonist Activity

The present inventors considered that the activity might be improved by modifying the N-terminal region. Therefore, to study the correlation between the structure of the N-terminal acyl group and GPR54 agonist activity, the present inventors prepared, in addition to compound 6, compounds 20 -32 and 35-39 having substituents shown in the following Table III as $R^y$ of a pentapeptide derivative represented by $R^y$—CO-Phe-Gly-Leu-Arg-Trp-NH$_2$ (SEQ ID NO: 27).

TABLE III
R$^y$ =
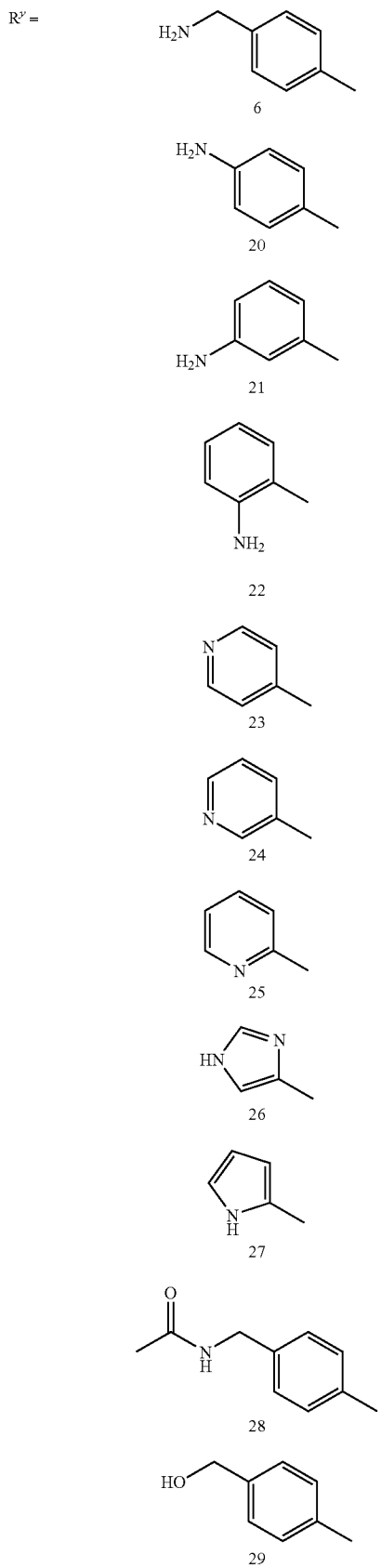
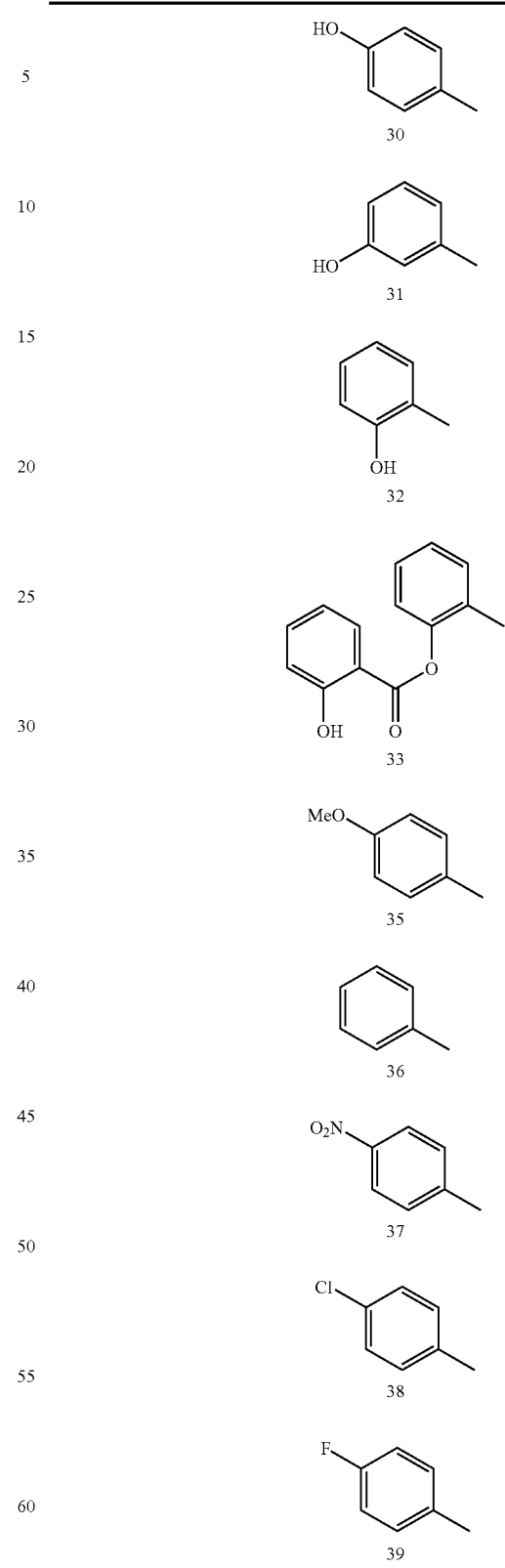
Compound 8 and compounds having the substituents shown in the above Table III were obtained according to the following method.

Production Example 1

Production of Compound 6

4-(aminomethyl)benzoyl-Phe-Gly-Leu-Arg-Trp-NH$_2$ (SEQ ID NO: 4)

(1) Synthesis of Protected Polypeptide Resin
After Fmoc group was removed from Fmoc-Rink amide resin with 20% piperidine/DMF, Fmoc-Trp-OH (5 eq) was added thereto, and the mixture was condensed in DMF according to the DIPCDI-HOBt method.
(2) Introduction of Each Amino Acid
In the same manner, Arg(Pbf), Leu, Gly, Phe and 4-(aminomethyl)benzoic acid residue were sequentially introduced into the resin to give polypeptide resins protected by a protecting group.
(3) Deprotection, and Separation and Purification of Polypeptide from Resin
The above-mentioned N-terminal modified polypeptide resin was reacted with TFA-thioanisole-m-cresol-1,2-ethanedithiol-TMSBr (115:16:75:75:24) at 0° C. for 1 hr. The resin was filtered off from the reaction mixture and washed twice with TFA. The filtrate and washing solution were combined and water-cooled dry ether was added thereto. The resulting precipitate was separated from the supernatant by centrifugal precipitation and decantation. The obtained residue was washed with cool ether and dissolved in a 0.1% TFA water-acetonitrile mixture. The aqueous solution was purified by a large preparative HPLC (Cosmosil 5C18 AR-II column: acetonitrile-water) to give polypeptide having a single peak, which was then freeze-dried. The purity was confirmed by HPLC.

Production Example 2

Production of Compound 8

4-(aminomethyl)benzoyl-Nal(2)-Gly-Leu-Arg-Trp-NH$_2$ (SEQ ID NO: 5)

8 was produced by a method similar to that of Production Example 1 except that L-3-(2-naphthyl)alanine was used instead of phenylalanine.

Production Example 3

Production of Compound 20

4-aminobenzoyl-Phe-Gly-Leu-Arg-Trp-NH$_2$ (SEQ ID NO: 6)

20 was produced by a method similar to that of Production Example 1 except that 4-aminobenzoic acid was used instead of 4-(aminomethyl)benzoic acid.

Production Example 4

Production of Compound 21

3-aminobenzoyl-Phe-Gly-Leu-Arg-Trp-NH$_2$ (SEQ ID NO: 7)

21 was produced by a method similar to that of Production Example 1 except that 3-aminobenzoic acid was used instead of 4-(aminomethyl)benzoic acid.

Production Example 5

Production of Compound 22

2-aminobenzoyl-Phe-Gly-Leu-Arg-Trp-NH$_2$ (SEQ ID NO: 8)

22 was produced by a method similar to that of Production Example 1 except that 2-aminobenzoic acid was used instead of 4-(aminomethyl)benzoic acid.

Production Example 6

Production of Compound 23

4-pyridylcarbonyl-Phe-Gly-Leu-Arg-Trp-NH$_2$ (SEQ ID NO: 9)

23 was produced by a method similar to that of Production Example 1 except that nicotinic acid was used instead of 4-(aminomethyl)benzoic acid.

Production Example 7

Production of Compound 24

3-pyridylcarbonyl-Phe-Gly-Leu-Arg-Trp-NH$_2$ (SEQ ID NO: 10)

24 was produced by a method similar to that of Production Example 1 except that nicotinic acid was used instead of 4-(aminomethyl)benzoic acid.

Production Example 8

Production of Compound 25

2-pyridylcarbonyl-Phe-Gly-Leu-Arg-Trp-NH$_2$ (SEQ ID NO: 11)

25 was produced by a method similar to that of Production Example 1 except that picoline acid was used instead of 4-(aminomethyl)benzoic acid.

Production Example 9

Production of Compound 26

4-imidazolylcarbonyl-Phe-Gly-Leu-Arg-Trp-NH$_2$ (SEQ ID NO: 12)

26 was produced by a method similar to that of Production Example 1 except that 4-imidazolecarboxylic acid was used instead of 4-(aminomethyl)benzoic acid.

Production Example 10

Production of Compound 27

2-pyrrolylcarbonyl-Phe-Gly-Leu-Arg-Trp-NH$_2$ (SEQ ID NO: 13)

27 was produced by a method similar to that of Production Example 1 except that 2-pyrrole carboxylic acid was used instead of 4-(aminomethyl)benzoic acid.

Production Example 11

Production of Compound 28

N-acetyl-4-(aminomethyl)benzoyl-Phe-Gly-Leu-Arg-Trp-NH$_2$ (SEQ ID NO: 14)

28 was produced by a method similar to that of Production Example 1 except that benzoic acid anhydride (10 eq.) was reacted in the presence of DIPEA after condensation of 4-(aminomethyl)benzoic acid residue.

Production Example 12

Production of Compound 29

4-(hydroxymethyl)benzoyl-Phe-Gly-Leu-Arg-Trp-NH$_2$ (SEQ ID NO: 15)

29 was produced by a method similar to that of Production Example 1 except that 4-(hydroxymethyl)benzoic acid was used instead of 4-(aminomethyl)benzoic acid.

Production Example 13

Production of Compound 30

4-hydroxybenzoyl-Phe-Gly-Leu-Arg-Trp-NH$_2$ (SEQ ID NO: 16)

30 was produced by a method similar to that of Production Example 1 except that 4-hydroxybenzoic acid was used instead of 4-(aminomethyl)benzoic acid.

Production Example 14

Production of Compound 31

3-hydroxybenzoyl-Phe-Gly-Leu-Arg-Trp-NH$_2$ (SEQ ID NO: 17)

31 was produced by a method similar to that of Production Example 1 except that 3-hydroxybenzoic acid was used instead of 4-(aminomethyl)benzoic acid.

Production Example 15

Production of Compounds 32 and 33

2-hydroxybenzoyl-Phe-Gly-Leu-Arg-Trp-NH$_2$ (SEQ ID NO: 18)

2-hydroxyphenylcarbonyloxybenzoyl-Phe-Gly-Leu-Arg-Trp-NH$_2$ (SEQ ID NO: 19)

32 was produced by a method similar to that of Production Example 1 except that salicylic acid was used instead of 4-(aminomethyl)benzoic acid. Compound 33 was obtained as a byproduct of compound 32.

Production Example 16

Production of Compound 35

4-methoxybenzoyl-Phe-Gly-Leu-Arg-Trp-NH$_2$ (SEQ ID NO: 20)

35 was produced by a method similar to that of Production Example 1 except that 4-anisic acid was used instead of 4-(aminomethyl)benzoic acid.

Production Example 17

Production of Compound 36 benzoyl-Phe-Gly-Leu-Arg-Trp-NH$_2$ (SEQ ID NO: 21)

36 was produced by a method similar to that of Production Example 1 except that benzoic acid was used instead of 4-(aminomethyl)benzoic acid.

Production Example 18

Production of Compound 37

4-nitrobenzoyl-Phe-Gly-Leu-Arg-Trp-NH$_2$ (SEQ ID NO: 22)

37 was produced by a method similar to that of Production Example 1 except that 4-nitrobenzoic acid was used instead of 4-(aminomethyl)benzoic acid.

Production Example 19

Production of Compound 38

4-chlorobenzoyl-Phe-Gly-Leu-Arg-Trp-NH$_2$ (SEQ ID NO: 23)

38 was produced by a method similar to that of Production Example 1 except that 4-chlorobenzoic acid was used instead of 4-(aminomethyl)benzoic acid.

Production Example 20

Production of Compound 39

4-fluorobenzoyl-Phe-Gly-Leu-Arg-Trp-NH$_2$ (SEQ ID NO: 24)

39 was produced by a method similar to that of Production Example 1 except that 4-fluorobenzoic acid was used instead of 4-(aminomethyl)benzoic acid.

Of these, the GPR54 agonistic activity of compounds 20, 25, 26, 27, 28, 30, 36, 37, 38 and 39 was measured. The results are shown in Table IV.

TABLE IV

| Compd | % activity[a] | EC$_{50}$ (nM)[a] | Q[a] | Compd | % activity[a] | EC$_{50}$ (M)[a] | Q[a] |
|---|---|---|---|---|---|---|---|
| 20 | 90 | 1.6 | 2.9 | 30 | 95 | 2.1 | 3.0 |
| 25 | 100 | 0.80 | 1.3 | 36 | 100 | 0.99 | 1.6 |
| 26 | 88 | 1.7 | 3.0 | 37 | 94 | 1.0 | 1.5 |

TABLE IV-continued

| Compd | % activity[a] | EC$_{50}$ (nM)[a] | Q[a] | Compd | % activity[a] | EC$_{50}$ (M)[a] | Q[a] |
|---|---|---|---|---|---|---|---|
| 27 | 96 | 2.0 | 1.7 | 38 | 92 | 1.3 | 1.3 |
| 28 | 100 | 0.99 | 1.6 | 39 | 96 | 0.69 | 0.63 |

[a]Values were calculated based on Flipr assay.

Particularly, when the activities of derivatives 37-39 having an electron-withdrawing group at the 4-position on the benzoyl ring were evaluated, all compounds showed an agonist activity stronger than that of unsubstituted benzoyl derivative 36. Particularly, 4-fluorobenzoyl derivative 39 showed about 1.6 times stronger activity than that of metastin (45-54), and about 2.5 times stronger activity than that of unsubstituted benzoyl derivative 36.

Since the tendency toward lower activity of m-position modified derivative was observed in a wide range of substituents, the tendency was considered to not stem from the presence of a substituent but rather, due to the lack of the m-position hydrogen atom. In other words, it was assumed that the hydrogen atom at the m-position contributed to the activity expression.

The chemical properties of the compounds obtained in this Example are shown in the following Table V.

TABLE V

| Compound | Over all yield (%)[a] | Formula | ISMS (MH)$^+$ Calcd. | ISMS (MH)$^+$ Found | $[\alpha]_D$ (c, temp. (° C.)) (in H$_2$O) |
|---|---|---|---|---|---|
| 6 | 19 | C$_{42}$H$_{56}$N$_{11}$O$_6$ | 811.0 | 811.0 | −15.4 (0.17, 24)[b] |
| 8 | 23 | C$_{46}$H$_{62}$N$_{11}$O$_6$ | 861.0 | 861.0 | −18.9 (0.36, 24)[b] |
| 20 | 30 | C$_{41}$H$_{54}$N$_{11}$O$_6$ | 796.9 | 797.0 | −20.1 (0.22, 24)[b] |
| 21 | 9 | C$_{41}$H$_{54}$N$_{11}$O$_6$ | 796.9 | 797.0 | −59.2 (0.17, 20)[b] |
| 22 | 42 | C$_{41}$H$_{54}$N$_{11}$O$_6$ | 796.9 | 797.0 | −38.5 (0.33, 20)[b] |
| 23 | 23 | C$_{40}$H$_{52}$N$_{11}$O$_6$ | 782.9 | 783.0 | −53.0 (0.16, 20)[b] |
| 24 | 27 | C$_{40}$H$_{52}$N$_{11}$O$_6$ | 782.9 | 783.0 | −20.9 (0.20, 19)[b] |
| 25 | 42 | C$_{40}$H$_{52}$N$_{11}$O$_6$ | 782.9 | 783.0 | −60.4 (0.20, 20)[b] |
| 26 | 38 | C$_{38}$H$_{50}$N$_{12}$O$_6$ | 771.9 | 772.0 | −11.4 (0.23, 24)[b] |
| 27 | 28 | C$_{39}$H$_{51}$N$_{11}$O$_6$ | 770.9 | 771.0 | −82.6 (0.24, 21)[b] |
| 28 | 36 | C$_{44}$H$_{57}$N$_{11}$O$_7$ | 853.0 | 853.0 | −14.3 (0.21, 23)[b] |
| 29 | 21 | C$_{42}$H$_{55}$N$_{10}$O$_7$ | 811.9 | 812.0 | −11.8 (0.31, 23)[b] |
| 30 | 32 | C$_{41}$H$_{52}$N$_{10}$O$_7$ | 797.9 | 798.0 | −81.9 (0.32, 22)[b] |
| 31 | 35 | C$_{41}$H$_{52}$N$_{10}$O$_7$ | 797.9 | 798.0 | −98.5 (0.27, 22)[b] |
| 32 | 27 | C$_{41}$H$_{53}$N$_{10}$O$_7$ | 797.9 | 798.0 | −80.0 (0.29, 22)[b] |
| 33 | 8 | C$_{49}$H$_{61}$N$_{11}$O$_8$ | 918.0 | 918.0 | −306.3 (0.13, 22)[b] |
| 35 | 42 | C$_{42}$H$_{55}$N$_{10}$O$_7$ | 811.9 | 812.0 | −15.0 (0.27, 21)[b] |
| 36 | 44 | C$_{41}$H$_{53}$N$_{10}$O$_6$ | 781.9 | 782.0 | −72.1 (0.25, 21)[b] |
| 37 | 13 | C$_{41}$H$_{51}$N$_{11}$O$_8$ | 826.9 | 827.0 | −41.3 (0.14, 21)[c] |
| 38 | 51 | C$_{41}$H$_{52}$ClN$_{10}$O$_6$ | 816.4 | 816.0 | −34.0 (0.33, 22)[c] |
| 39 | 42 | C$_{41}$H$_{52}$FN$_{10}$O$_6$ | 799.9 | 800.0 | −23.2 (0.38, 22)[b] |

[a]Yields were calculated from the corresponding resin.
[b]in H$_2$O.
[c]in MeOH Sequence Listing Free Text SEQ ID NO: 1 represents the amino acid sequence of metastin (45-54).
SEQ ID NO: 2 represents the amino acid sequence of FM052a1.
SEQ ID NO: 3 represents the amino acid sequence of FM053a2.
SEQ ID NO: 4 represents the amino acid sequence of compound 6.
SEQ ID NO: 5 represents the amino acid sequence of compound 8.
SEQ ID NO: 6 represents the amino acid sequence of compound 20.
SEQ ID NO: 7 represents the amino acid sequence of compound 21.
SEQ ID NO: 8 represents the amino acid sequence of compound 22.
SEQ ID NO: 9 represents the amino acid sequence of compound 23.
SEQ ID NO: 10 represents the amino acid sequence of compound 24.
SEQ ID NO: 11 represents the amino acid sequence of compound 25.
SEQ ID NO: 12 represents the amino acid sequence of compound 26.
SEQ ID NO: 13 represents the amino acid sequence of compound 27.
SEQ ID NO: 14 represents the amino acid sequence of compound 28.
SEQ ID NO: 15 represents the amino acid sequence of compound 29.
SEQ ID NO: 16 represents the amino acid sequence of compound 30.
SEQ ID NO: 17 represents the amino acid sequence of compound 31.
SEQ ID NO: 18 represents the amino acid sequence of compound 32.
SEQ ID NO: 19 represents the amino acid sequence of compound 33.
SEQ ID NO: 20 represents the amino acid sequence of compound 35.
SEQ ID NO: 21 represents the amino acid sequence of compound 36.
SEQ ID NO: 22 represents the amino acid sequence of compound 37.
SEQ ID NO: 23 represents the amino acid sequence of compound 38.
SEQ ID NO: 24 represents the amino acid sequence of compound 39.

Industrial Field of Utilization

According to the present invention, a compound having a low-molecular weight and a superior GPR54 agonist activity can be provided. The compound of the present invention specifically binds to a seven-transmembrane receptor, GPR54, to activate the receptor, and enhances the action of its endogenous ligand, metastin (aka: kisspeptin). The compound of the present invention has a drastically reduced molecular weight as compared to natural metastin, and strikingly enhanced GPR54 agonist activity. In addition, since the compound of the present invention is modified to be not susceptible to degradation by peptidase in the body, it can efficiently act as a GPR54 agonist.

A pharmaceutical composition containing the compound of the present invention can be effectively used as a cancer metastasis suppressor as well as an agent for the prophylaxis or treatment of infertility and abnormal secretory regulation of sex hormones and gonadotropic hormones, via a GPR54 receptor agonist action.

In addition, since it has been clarified that metastin suppressively acts on CXCR4-chemokine receptor (CXCR4) deeply involved in cancer metastasis or growth, rheumatoid arthritis, lung fibrosis and HIV infection, the pharmaceutical composition of the present invention is expected to be effective as a prophylactic or therapeutic agent for these diseases. It is also possible to utilize a pharmaceutical composition containing the compound of the present invention instead of CXCR4 antagonists and CXCR4 monoclonal antibodies feared to cause side effects.

The present invention is based on a patent application 2006-122305 filed in Japan, the contents of which are encompassed in full in the present specification.

The invention claimed is:

1. A compound represented by the following formula (1):

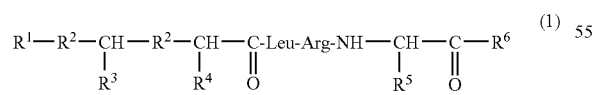

wherein $R^1$ is any one kind selected from the group consisting of a 2-pyrrolyl group, a 4-methoxyphenyl group, a 4-chlorophenyl group, and a 4-fluorophenyl group $R^2$ is any one kind selected from the group consisting of —CO—NH—, —CH=CH—, —SO$_2$—NH— and —CH$_2$—NH—;

$R^3$ is a methyl group having an aromatic group or a cycloalkyl group;

$R^4$ is any one kind selected from the group consisting of a hydrogen atom, a methyl group, a phenyl group and a benzyl group;

when $R^2$ is —CO—NH—, —SO$_2$—NH— or —CH$_2$—NH— and the nitrogen atom of $R^2$ is bonded to $R^4$, then —$R^2$—CHR$^4$— optionally forms

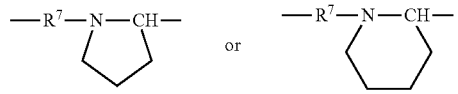

wherein $R^7$ is —CO—, —SO$_2$— or —CH$_2$—;

$R^5$ is a methyl group having an aromatic group; and $R^6$ is an amino group or an N-alkyl-substituted amino group.

2. The compound of claim 1, wherein $R^3$ is any one kind selected from the group consisting of a benzyl group, a naphthylmethyl group and a cyclohexylmethyl group.

3. The compound of claim 1, wherein $R^4$ is a hydrogen atom.

4. The compound of claim 1, wherein $R^5$ is any one kind selected from the group consisting of a 3-indolylmethyl group, a naphthylmethyl group, a benzyl group and a hydroxybenzyl group.

5. A pharmaceutical composition comprising a compound of claim 1, and a pharmaceutically acceptable excipient, a diluent or a carrier.

6. The pharmaceutical composition of claim 5, which is used for a disease for which activation of GPR54 is effective for the treatment thereof.

7. A cancer metastasis suppressor comprising the pharmaceutical composition of claim 6.

8. The metastasis suppressor of claim 7, wherein the cancer is melanoma or pancreatic cancer.

9. A therapeutic agent for infertility comprising the pharmaceutical composition of claim 6.

* * * * *

UNITED STATES PATENT AND TRADEMARK OFFICE
CERTIFICATE OF CORRECTION

PATENT NO. : 8,183,212 B2
APPLICATION NO. : 12/298200
DATED : May 22, 2012
INVENTOR(S) : Fujii et al.

It is certified that error appears in the above-identified patent and that said Letters Patent is hereby corrected as shown below:

Title Page:

Item 73 in the Assignee's Name:

Please change "Takeda Phamaceutical Company Limited" to "Takeda Pharmaceutical Company Limited"

Signed and Sealed this
Sixth Day of November, 2012

David J. Kappos
*Director of the United States Patent and Trademark Office*

SEQUENCE LISTING

<160> NUMBER OF SEQ ID NOS: 27

<210> SEQ ID NO 1
<211> LENGTH: 10
<212> TYPE: PRT
<213> ORGANISM: Homo sapiens
<220> FEATURE:
<223> OTHER INFORMATION: C-term amidated

<400> SEQUENCE: 1

Tyr Asn Trp Asn Ser Phe Gly Leu Arg Phe
1               5                   10

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: N,N-bis-(2-picolyl)aminomethyl-Phe
<220> FEATURE:
<223> OTHER INFORMATION: C-term amidated

<400> SEQUENCE: 2

Phe Gly Leu Arg Trp
1               5

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Guanidinomethyl-Phe
<220> FEATURE:
<223> OTHER INFORMATION: C-term amidated

<400> SEQUENCE: 3

Phe Gly Leu Arg Trp
1               5

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-(aminomethyl)benzoyl-Phe
<220> FEATURE:
<223> OTHER INFORMATION: C-term amidated

<400> SEQUENCE: 4

Phe Gly Leu Arg Trp
1               5

<210> SEQ ID NO 5
<211> LENGTH: 5

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-(aminomethyl)benzoyl-Nal(2)
<220> FEATURE:
<223> OTHER INFORMATION: C-term amidated

<400> SEQUENCE: 5

Xaa Gly Leu Arg Trp
1               5

<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-aminobenzoyl-Phe
<220> FEATURE:
<223> OTHER INFORMATION: C-term amidated

<400> SEQUENCE: 6

Phe Gly Leu Arg Trp
1               5

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-aminobenzoyl-Phe
<220> FEATURE:
<223> OTHER INFORMATION: C-term amidated

<400> SEQUENCE: 7

Phe Gly Leu Arg Trp
1               5

<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 2-aminobenzoyl-Phe
<220> FEATURE:
<223> OTHER INFORMATION: C-term amidated

<400> SEQUENCE: 8

Phe Gly Leu Arg Trp
1               5

<210> SEQ ID NO 9
<211> LENGTH: 5
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-pyridylcarbonyl-Phe
<220> FEATURE:
<223> OTHER INFORMATION: C-term amidated

<400> SEQUENCE: 9

Phe Gly Leu Arg Trp
1               5

<210> SEQ ID NO 10
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-pyridylcarbonyl-Phe
<220> FEATURE:
<223> OTHER INFORMATION: C-term amidated

<400> SEQUENCE: 10

Phe Gly Leu Arg Trp
1               5

<210> SEQ ID NO 11
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 2-pyridylcarbonyl-Phe
<220> FEATURE:
<223> OTHER INFORMATION: C-term amidated

<400> SEQUENCE: 11

Phe Gly Leu Arg Trp
1               5

<210> SEQ ID NO 12
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-imidazolylcarbonyl-Phe
<220> FEATURE:
<223> OTHER INFORMATION: C-term amidated

<400> SEQUENCE: 12

Phe Gly Leu Arg Trp
1               5

<210> SEQ ID NO 13
<211> LENGTH: 5
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 2-pyrrolylcarbonyl-Phe
<220> FEATURE:
<223> OTHER INFORMATION: C-term amidated

<400> SEQUENCE: 13

Phe Gly Leu Arg Trp
1               5

<210> SEQ ID NO 14
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: N-acetyl-4-(aminomethyl)benzoyl-Phe
<220> FEATURE:
<223> OTHER INFORMATION: C-term amidated

<400> SEQUENCE: 14

Phe Gly Leu Arg Trp
1               5

<210> SEQ ID NO 15
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-(hydroxymethyl)benzoyl-Phe
<220> FEATURE:
<223> OTHER INFORMATION: C-term amidated

<400> SEQUENCE: 15

Phe Gly Leu Arg Trp
1               5

<210> SEQ ID NO 16
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-hydroxybenzoyl-Phe
<220> FEATURE:
<223> OTHER INFORMATION: C-term amidated

<400> SEQUENCE: 16

Phe Gly Leu Arg Trp
1               5

<210> SEQ ID NO 17
<211> LENGTH: 5
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-hydroxybenzoyl-Phe
<220> FEATURE:
<223> OTHER INFORMATION: C-term amidated

<400> SEQUENCE: 17

Phe Gly Leu Arg Trp
1               5

<210> SEQ ID NO 18
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 2-hydroxybenzoyl-Phe
<220> FEATURE:
<223> OTHER INFORMATION: C-term amidated

<400> SEQUENCE: 18

Phe Gly Leu Arg Trp
1               5

<210> SEQ ID NO 19
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 2-hydroxyphenylcarbonyloxybenzoyl-Phe
<220> FEATURE:
<223> OTHER INFORMATION: C-term amidated

<400> SEQUENCE: 19

Phe Gly Leu Arg Trp
1               5

<210> SEQ ID NO 20
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-methoxybenzoyl-Phe
<220> FEATURE:
<223> OTHER INFORMATION: C-term amidated

<400> SEQUENCE: 20

Phe Gly Leu Arg Trp
1               5

<210> SEQ ID NO 21
<211> LENGTH: 5
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Benzoyl-Phe
<220> FEATURE:
<223> OTHER INFORMATION: C-term amidated

<400> SEQUENCE: 21

Phe Gly Leu Arg Trp
1               5

<210> SEQ ID NO 22
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-nitrobenzoyl-Phe
<220> FEATURE:
<223> OTHER INFORMATION: C-term amidated

<400> SEQUENCE: 22

Phe Gly Leu Arg Trp
1               5

<210> SEQ ID NO 23
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-chrolobenzoyl-Phe
<220> FEATURE:
<223> OTHER INFORMATION: C-term amidated

<400> SEQUENCE: 23

Phe Gly Leu Arg Trp
1               5

<210> SEQ ID NO 24
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-fluorobenzoyl-Phe
<220> FEATURE:
<223> OTHER INFORMATION: C-term amidated

<400> SEQUENCE: 24

Phe Gly Leu Arg Trp
1               5

<210> SEQ ID NO 25
<211> LENGTH: 5
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 2-pyrrolyl-Phe, 4-methoxyphenyl-Phe, 4-
      chlorophenyl-Phe or 4-fluorophenyl-Phe
<220> FEATURE:
<223> OTHER INFORMATION: C-term amidated

<400> SEQUENCE: 25

Phe Gly Leu Arg Trp
1               5

<210> SEQ ID NO 26
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: N,N-bis-(2-picolyl)aminomethyl-Phe,
      guanidinomethyl-Phe or aminomethyl-Phe
<220> FEATURE:
<223> OTHER INFORMATION: C-term amidated

<400> SEQUENCE: 26

Phe Gly Leu Arg Trp
1               5

<210> SEQ ID NO 27
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term is modified by various chemical
      compounds; see specification as filed for preferred structures
<220> FEATURE:
<223> OTHER INFORMATION: C-term amidated

<400> SEQUENCE: 27

Phe Gly Leu Arg Trp
1               5
```